(12) United States Patent
Berry

(10) Patent No.: US 11,458,183 B1
(45) Date of Patent: *Oct. 4, 2022

(54) **INDUCING GRANULATION TISSUE IN THIRD-DEGREE SKIN BURNS USING TOPICAL *HAMELIA PATENS* EXTRACT**

(71) Applicant: Don Wayne Berry, Georgetown, TX (US)

(72) Inventor: Don Wayne Berry, Georgetown, TX (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/602,156

(22) Filed: Aug. 15, 2019

Related U.S. Application Data

(63) Continuation-in-part of application No. 15/732,771, filed on Dec. 26, 2017, now Pat. No. 10,383,908.

(60) Provisional application No. 62/498,672, filed on Jan. 3, 2017.

(51) Int. Cl.
| | | |
|---|---|---|
| *A61K 36/74* | (2006.01) | |
| *A61P 17/02* | (2006.01) | |
| *A61K 9/127* | (2006.01) | |
| *A61K 9/107* | (2006.01) | |
| *A61K 9/00* | (2006.01) | |

(52) U.S. Cl.
CPC ............ *A61K 36/74* (2013.01); *A61K 9/0014* (2013.01); *A61K 9/107* (2013.01); *A61K 9/127* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 10,383,908 B1 * | 8/2019 | Berry | A61K 9/127 |
| 2011/0086088 A1 * | 4/2011 | Berry | A61P 17/00 |
| | | | 424/450 |

OTHER PUBLICATIONS

Taylor (The Healing Powers of Rainforest Herbs. Square One Publishers, 2005, pp. 144, 145, and 417-420).*

* cited by examiner

*Primary Examiner* — Susan Hoffman
(74) *Attorney, Agent, or Firm* — Chris Whewell

(57) ABSTRACT

Methods are provided for inducing granulation tissue on chronic third-degree post-escharotomy burn wounds present on the skin of a mammalian subject, which includes human subjects. A method according to the disclosure comprises contacting a third-degree burn wound with an extract of *Hamelia patens*, in combination with a dermatologically-acceptable carrier. Methods according to the disclosure are applicable to chemically-induced, electrically-induced, and thermally-induced third-degree burn wounds on skin.

11 Claims, No Drawings

INDUCING GRANULATION TISSUE IN THIRD-DEGREE SKIN BURNS USING TOPICAL *HAMELIA PATENS* EXTRACT

TECHNICAL FIELD

This invention relates generally to burned skin on human subjects. More particularly, it relates to topical compositions comprising an extract of the plant species *Hamelia patens*, and in some aspects to the use of such compositions in treating human skin which has been exposed to thermal energy of sufficient intensity to cause third-degree burns.

BACKGROUND OF THE INVENTION

The statements in this background section merely provide background information related to the present disclosure and may not constitute prior art.

Various compositions and materials have been proffered in the past as being beneficial for treating the skin of human subjects that was exposed to intense heat and severely burned. Severe skin burns can result from direct exposure to heat, such as from when a person is trapped in a fire, or when their person is literally on fire, perhaps by virtue of having petrol or other hydrocarbon on their body, which somehow becomes ignited. Severe thermally-induced skin burns can also result from skin contact with hot liquids or solids, including without limitation liquids such as steam and hot oils, and hot solids such as red-hot iron and ceramics. Chemically-induced severe skin burns can result from contact with strong acids, strong alkalis, phenols, cresols and many other known inorganic and organic compounds. Deep tissue necrosis from chemical burns often results from chemical exposures. Severe burns to human skin can also result from skin exposure to electricity, including radio frequency (RF) energy.

Burns on human skin which are thermally-induced or caused by heat are classified into three types: first-degree skin burns, second-degree skin burns, and third-degree skin burns. It is recognized in the art that first-degree skin burns are those on the skin which are limited in depth to only the epidermis, and second-degree thermal skin burns (partial-thickness burns) are those which further involve damage to the papillary dermis. Second-degree thermal skin burns typically heal within about two weeks time, with little to no scarring. It is accepted in the art that the healing of second-degree burns occurs from epidermal cells that line or surround the sweat gland ducts and hair follicles, which cells grow towards the surface of the epidermis and towards other similarly growing cells from adjacent sweat gland ducts and hair follicles. Some second-degree burns can partially involve deeper layers of the dermis and require more than two weeks to heal, since, in such deeper second-degree burns, healing only occurs from the cells lining or surrounding the hair follicles.

Various topical treatments have been employed and marketed for treating first and second-degree thermal skin burns. Commonly-used remedies include simple soaking the affected area or burn wound in cold water, and topical application of various crèmes, lotions, ointments, and the like. In some formulations, local anesthetics including without limitation lidocaine are present in a topical formulation applied directly to skin for relief from pain associated with the burned area. Some topical formulations include antibiotics such as silver sulfadiazine; however, a few other known topical anti-biotic formulations have been employed. Another common remedy is for the person to systemically ingest a non-steroidal anti-inflammatory medicament, such as acetaminophen or ibuprofen. First-degree and second-degree burns typically heal on their own, with time.

Third-degree skin burns are a completely different story than first-degree or second-degree skin burns. Third-degree burns result in en masse protein denaturation and coagulative necrosis, mostly due to the brute-force effect of pyrolysis-like oxidative reactions caused to occur when an intense source of heat is acutely present in close proximity to, or contact with the skin. Third-degree burn scenarios are somewhat analogous to the situation in which cattle are branded with a red-hot branding iron, or the changes experienced by a corpse during the early moments of a cremation process.

By definition, third-degree burns extend entirely through all dermal layers and into the underlying muscular and/or fatty tissues. This results in the extreme complication whereby the body can only heal third-degree burns from the periphery of the damaged regions. For cases where substantial portions of the human body experiences third-degree burns, this often means that healing is not possible; i.e., when there is essentially no undamaged tissue adjacent to a third-degree burn area, healing cannot occur. For this reason, it is generally accepted in the medical arts that third-degree burns require excision (escharectomy) and skin grafting.

Medical personnel use the measure of Total Body Surface Area (TBSA) involvement, which is an estimation of the surface area of the body affected by burns, to quantitatively describe the extent to which the body of an individual has been burned. It is generally accepted in the art that for adult subjects, a TBSA in the range of between about 20 to 25% requires intravenous fluid resuscitation. It is also generally accepted that subjects who have experienced third-degree burns having a TBSA of between about 30 to 40% may be in a fatal situation, absent any treatment. Moreover, persons having bodily burns with a TBSA greater than about 40% are prone to develop systemic complications including hypovolemia, infections, hypoalbuminemia, electrolyte deficiencies, metabolic acidosis, rhabdomyolysis, hemolysis, hypothermia and ileus, among others.

Prior to the present invention, there has been no known effective topical medicament useful for inducing formation of granulation tissue in third-degree burns on human skin. The present invention is also applicable to all mammalian skin, using the same treatment specifications and/or regimens herein described.

SUMMARY OF THE INVENTION

Provided are compositions and methods useful for inducing islands of granulation tissue in a third-degree burn wound on the skin of a human subject by contacting *Hamelia patens* extract to said wound. In some embodiments the *Hamelia patens* extract is provided in combination with a dermatologically-acceptable carrier. Wounds treated according to methods of the present disclosure heal flat and smooth, without keloid formation or subsequent dehiscence. The presence of induced granulation tissue is visually-observable in some embodiments in as little as 48 hours from initial application of *Hamelia patens* extract to a third-degree burn wound on the skin of a human subject according to this disclosure.

DETAILED DESCRIPTION

This disclosure concerns the plant known as *Hamelia patens*, its parts, and extracts or extract concentrates prepared therefrom, constituents thereof, and their topical use in treating and healing third-degree burns on human skin. *Hamelia patens* is a perennial shrub or shrub-like plant that is sometimes referred to as Scarlet Bush, Firebush, and Texas Firecracker, among other common names. *Hamelia patens* grows in Florida, Texas, and other southern and southwestern states, and is also distributed throughout parts of central and south America. The plant has a woody stem and roots, broad leaves and at maturity produces bright red berries. An extract provided in accordance with this disclosure is produced using any combination of parts of the *Hamelia patens* plant, of any of its sub-species, which parts are selected from the group consisting of: its roots, stems, leaves, and fruit. In some embodiments, only the leaves are employed in preparing the extract.

A *Hamelia patens* extract in some embodiments according to this disclosure is provided by first picking leaves from a sub-species of the plant, the sub-species in some non-limiting embodiments being *Hamelia patens* jacq. In one exemplary embodiment about 509 grams of freshly-picked leaves of *Hamelia patens* jacq. were procured from *Hamelia patens* jacq. grown in Texas. Stems were removed from the leaves and the leafy material was cut transversely into strips. The cut leafy material was combined with about 475 milliliters of CETAPHIL® gentle skin cleanser (Galderma Laboratories) in a covered one-liter beaker and blended using a stirring rod until the leafy material was evenly distributed throughout the bulk of the composition. The contents of the beaker were heated to 65.5 degrees Centigrade for 30 minutes with frequent stirring. During the course of the heating the leaves turned to a dull green with a brown cast. At the end of the 30 minutes the leafy material was compacted using a potato masher, to squeeze more of the plant-borne matter from the leaves and into the bulk of the composition. Finally, the beaker's contents were poured through a stainless steel screen, of sufficient mesh to separate the solid matter including leaves from the liquid portion, which liquid portion itself was subsequently strained through cheesecloth, thus providing a liquid *Hamelia patens* extract suitable for topical application to human skin to induce formation of granulation tissue in a third-degree burn wound thereon. As used herein, "human skin" includes any skin located on any part of the body of a human subject.

In other embodiments useful for providing a *Hamelia patens* extract, a protic solvent such as water, or a lower alcohol (any C1-C4 alcohol), or a mixture comprising a plurality of lower alcohols, or blends comprising one or a plurality of lower alcohols and water, when miscible, in any relative proportions, is employed as a liquid solvent into which the constituents of *Hamelia patens* are extracted from the plant. In some embodiments the lower alcohol is any alcohol selected from any C1-C4 alcohol, including any mixtures thereof, independently selected to be present in any desired proportion. In some embodiments a water/alcohol mixture containing any amount in the range from about 5% to about 10% by volume of the alcohol in water is used as a solvent. Various extraction techniques known in the art may be employed, including percolation, soxhlet extraction, and other extraction techniques, including those employing supercritical carbon dioxide. In one embodiment about 500 grams of dried *Hamelia patens* leaves ground to a coarse powder are combined with about 500 ml of a mixture that is 10% by volume of ethanol and 90% by volume of water, in a suitable vessel and heated to about 65 degrees Centigrade for 30 minutes. In alternate embodiments, the solvent is maintained at room temperature and the mixture of plant matter and solvent is permitted to percolate for an extended time, of 24 hours. In other embodiments, a longer extraction time in the range of between about 24 hours and about 72 hours is employed. The resulting solution from such heating, percolation, or other extraction technique is filtered and optionally centrifuged to provide a liquid solution *Hamelia patens* extract. This solution extract in some embodiments is applied as-is to human skin to induce formation of granulation tissue in, on, or at the location of a third-degree burn wound present. In alternate embodiments various other materials may be combined with such solution extract to form skin creams, lotions, salves, ointments, etc., as described below prior to its application to human skin to induce formation of granulation tissue in, on, or at the location of a third-degree burn wound present. In some embodiments, the solvent present in such a liquid solution extract is removed using techniques known to those skilled in the art (including reduced pressure distillation, flash evaporation, a rotary evaporator, nitrogen sweep, etc.) to yield an extract in the form of a dry powder, crystalline, amorphous, or other solid, or semi-solid form. In some embodiments, the temperature of the liquid solvent extract is not permitted to exceed about 50 degrees Centigrade during solvent removal. In one embodiment when a solvent comprising 10% by volume ethanol in 90% by volume water is employed at room temperature in a percolation lasting about 24 hours, the yield of dry *Hamelia patens* extract provided following solvent removal amounts to about 7% by weight based on the weight of the fresh-cut *Hamelia patens* leaves employed. Typically by such processing the yield of *Hamelia patens* extract ranges from between about 2% to about 8% by weight based on the weight of the plant matter used. While an extract of the *Hamelia patens* plant is in some embodiments crystalline in nature, it is understood by those skilled in the art that extracts of the plant *Hamelia patens* obtained following solvent removal may not always be perfectly crystalline or powdered crystalline in nature owing to variation among individual plants' growing condition, time of harvest, and genetics, which can impact the quantity of polymeric residues present or other aspects of composition which affect crystallinity. Thus, in some embodiments a non-completely-crystalline residue or extract may be obtained from an extraction of a *Hamelia patens* plant, such as extracts comprised of or which include amorphous or partially-gummy residues or components; however in general such non-completely crystalline extracts obtained are viewed as being equivalent to a crystalline extract for purposes of this disclosure and these forms are all to be treated herein as being included in the term *Hamelia patens* extract where the context does not otherwise exclude non-crystalline or gummy or other residues or components. Thus, the words *Hamelia patens* extract refers to crystalline, semi-crystalline, amorphous, and any other physically observable form of the material which results from an extraction of the *Hamelia patens* plant that is free from the solvent that was used to extract it from the plant matter. A *Hamelia patens* extract when specified herein can be the material obtained from *Hamelia patens* when the plant is extracted with either water, or other solvents including aqueous alcoholic solvents, and can be mixtures of extracts obtained using various solvents. In some embodiments the *Hamelia patens* extract is an aqueous extract, i.e., produced as a result of the plant matter being extracted with water. In other embodiments the *Hamelia patens* extract is an aqueous alcohol extract. In some embodiments the *Hamelia patens* extract is mixture of extracts from both aqueous and aqueous alcoholic, or alcoholic extracts in any desired or selected proportion.

Compositions according to some embodiments of the disclosure are prepared by mixing a *Hamelia patens* extract with various other materials, as desired, such other materials collectively comprising a dermatologically-acceptable carrier. In some embodiments the crystalline *Hamelia patens* extract is ground with a mortar or otherwise pulverized, or liquefied by addition of any selected suitable solvent, and combined with or formulated into a skin crème or skin lotion, salve, etc. at any desired concentration, to provide a medicament suitable for topical application to human skin in which the concentration of *Hamelia patens* extract is preselected to be any concentration between about 0.05% by weight and about 85% by weight based on the weight of the final medicament composition, including all weight percentages and ranges of weight percentages therebetween. In some embodiments, the exact concentration selected is at the discretion of a physician, as it is sometimes desirable to adjust concentrations and topical application frequency to suit the needs of a particular patient.

In some embodiments a crystalline *Hamelia patens* extract is blended with at least one other material that is a solid or liquid at room temperature, in any suitable or desired amount, in order to provide a *Hamelia patens* extract concentrate that can be used to conveniently provide finished topical medicaments by combination with other materials, as desired. Such at least one other material in some embodiments comprises a material selected from the group consisting of: silicates, aluminosilicates and silica present in effective flow-enhancing amounts to enable the *Hamelia patens* extract to flow freely when poured. In other embodiments, a *Hamelia patens* extract according to the disclosure is combined with a solvent, to provide a solution that comprises a *Hamelia patens* extract concentrate, in which *Hamelia patens* extract is present in any amount between about 1% by weight based on the total weight of the concentrate, up to the saturation limit of the *Hamelia patens* extract in the solvent employed, at ambient conditions.

In some embodiments a *Hamelia patens* extract is combined with a glyceryl ester based oil that is either plant-derived or animal-derived, and in some embodiments with any pre-selected mixture of glyceryl ester based oils. Suitable exemplary glyceryl ester based oils include without limitation oils such as soybean oil, coconut oil, palm oil, palm kernel oil, corn oil, olive oil, sunflower oil, safflower oil, cottonseed oil, rape oil including Canadian oil low acid, almond oil, sesame oil, peanut oil, beef tallow, lard, emu oil, butterfat, and mixtures thereof in any selected proportion. A composition according to some embodiments of this disclosure includes a *Hamelia patens* extract in combination with a glyceryl ester oil (alternately mixtures including a plurality of such oils, each present in any proportion), wherein the *Hamelia patens* extract is present in any amount between 1% by weight to 85% by weight, based on the total weight of the composition, including all percentages by weight and ranges of percentages by weight therebetween. The presence of a fatty acid glyceryl ester oil as a vehicle in general is capable of facilitating or assisting in transdermal passage of one or more component materials present in *Hamelia patens* extract into the tissues associated with a third-degree burn. A glyceryl ester oil can also in some embodiments be used in place of water, alcohol or a mixture of water and alcohol as described herein, as the solvent into which a *Hamelia patens* extract is initially made from the plant material, such glyceryl ester oil solvent being subsequently separated from the constituents of the *Hamelia patens* that were extracted, if desired, using conventional techniques as reduced pressure distillation, molecular distillation, chromatography, etc.

Thus, instead of steeping, percolating, etc. *Hamelia patens* plant parts in a solvent of water, alcohol, or an alcohol-water mixture, any glyceryl ester oil including without limitation those listed above, can be employed as a solvent in the extraction process. Following extraction, the glyceryl ester oil laden with constituent materials of the *Hamelia patens* plant can be filtered and then used directly as an ingredient in a topical medicament composition according to some embodiments of the present invention.

In other embodiments, a *Hamelia patens* extract is combined with water and optionally instead with any water/alcohol mixture including those described above to provide a solubilized form of *Hamelia patens* extract useful to provide topical medicament compositions according to the disclosure for inducing granulation tissue in third-degree burns.

Compositions according to some embodiments of the disclosure include a *Hamelia patens* extract in combination with water, in alternate embodiments in combination with alcohol, in alternate embodiments in combination with water/alcohol mixtures, in alternate embodiments in combination with glyceryl ester oil(s) as solvent, and in these embodiments the amount of *Hamelia patens* extract (crystalline or otherwise) is present in any desired amount between 1% by weight and up to the solubility limit of the solvent selected, which can be as high as 85% by weight of *Hamelia patens* extract, based on the total weight of the composition, including all percentages by weight and ranges of percentages by weight therebetween. In different embodiments any C1 to C4 alcohol (including any mixtures thereof in any proportion) are used, as solvent, either mixed with water in any chosen proportion, or anhydrous or substantially anhydrous. Any vegetable oil or plant-derived glyceryl ester oil may also be used as a solvent for making an extract of *Hamelia patens* using the same techniques as for the use of water, alcohols, or water-alcohol mixtures.

In another exemplary embodiment, about a one-liter volume of cut *Hamelia patens* leaves are compressed and combined with about 125 ml of petrolatum, the mixture being heated to any temperature in the range of between about sixty (60) degrees Centigrade and about eighty (80) degrees Centigrade for about 10 minutes. This provides a hydrocarbon base containing *Hamelia patens* extract that is in some embodiments applied directly to human skin, or alternately is useful in preparing compositions according to other embodiments of this disclosure comprising other ingredients known to be used or useful in dermatologically-acceptable carriers. In some embodiment this petrolatum-borne extract is combined with effective amounts of one (and alternately any number more than one) of an anti-inflammatory, anti-oxidant, and/or anti-bacterial material to provide an enhanced *Hamelia patens* extract. Such a petrolatum-borne *Hamelia patens* extract is easy to handle enabling quick and ready blending with other materials. In other embodiments, a powdered crystalline *Hamelia patens* extract is combined with petrolatum and heated with agitation to provide a composition according to the disclosure wherein the extract of *Hamelia patens* is present in any amount between 1% by weight to 85% by weight, based on the total weight of the petrolatum-based composition, including all percentages by weight and ranges of percentages by weight therebetween.

In another embodiment, a liquid solution *Hamelia patens* extract, (for example prepared by combining *Hamelia patens* plant parts with a solvent and percolating at about 60 degrees Centigrade) wherein the solvent is a 90% water/10% ethanol (by volume) mixture is combined with any vegetable oil or any glycerol ester oil to provide a mixture that is heated with stirring sufficiently to simmer off the water and alcohol present, under ambient or reduced pressure, causing the *Hamelia patens* extract to be taken up into the oil. For such embodiments, the quantity of water/ethanol extract and oil used are selected to provide an amount of *Hamelia patens* extract present in the final composition in any amount between 1% by weight and 85% by weight, based on the total weight of the composition, including all percentages by weight and ranges of percentages by weight therebetween. In alternate embodiments, one begins with a crystalline *Hamelia patens* extract and dissolves it in water/ethanol mixture comprising about 10% ethanol by volume and once dissolved, this mixture is combined with any desired amount of oil, the water/ethanol present is subsequently removed to afford an oil-borne *Hamelia patens* extract.

Thus, the present disclosure in various embodiments provides compositions comprising a crystalline *Hamelia patens* extract in combination with at least one material selected from the group consisting of: water, water/alcohol mixtures, hydrocarbons (petrolatum) and ester-type fats or oils, wherein the *Hamelia patens* extract is present in any amount between 0.05% by weight to 85% by weight, based on the total weight of the composition, including all percentages by weight and ranges of percentages by weight therebetween.

Crystalline or liquid (including aqueous, non-aqueous, alcoholic, hydrocarbon-based, and oil-borne) *Hamelia patens* extracts as provided herein may be further refined to isolate or concentrate any one, or more than one, of the compounds present in *Hamelia patens* using methods or techniques generally known to those skilled in the art including without limitation solvent extraction based on acid/base properties of the constituents, distillation, steam distillation, molecular distillation, and chromatography.

A *Hamelia patens* extract provided according to some embodiments of the disclosure contains at least any one compound, and in other embodiments contains any mixture comprising a plurality including any two or more than two of the following compounds: alkaloids, 2-alpha-hydroxyursolic acid, apigenin-7-o-beta d-glucuronide, aricine, catequine, 19-alphahydroxy Asiatic acid, 24-methylenecycloartane-3β-ol, 24-methylcycloart-24-en-3β-ol, 2 E-3,7,11,15,19-pentamethyl-2-eicosane-1-ol, ephedrine, flavonones, 2'-5-5'-7-tetrahydroxy-7-o-rutinoside, isomaruquine, isopteropodine, maruquine, the methyl ester of maruquine, mitraphylline, narirutin, narirutin (2r), narirutin (2s), oxindole alkaloids, oxindole aricine, palmirine, pigenin-7-o-beta D-glucuronide, pomolic acid, pteropodine, rumberine, rosmarinic acid, rotundic acid, rumberine, rutin, seneciophylline, β-sitos terol, speciophylline, stigmast-4-en-3-3-dione, stigmast-4-en-3-6-dione, stigmasterol, tannins, tormentic acid, uncarine F, and ursolic acid. In some embodiments, all of these compounds are present in a *Hamelia patens* extract useful to induce formation of granulation tissue in, on, or at the location of a third-degree burn wound present on human skin.

Accordingly, a *Hamelia patens* extract as provided in some embodiments contains alkaloids. In some embodiments alkaloids are present in a composition useful according to the disclosure in any amount between about 0.05% and about 30% by weight based on the total weight of the composition, including all weight percents and ranges of weight percents therebetween. A *Hamelia patens* extract as provided in some embodiments contains apigenin-7-o-beta d-glucuronide. In some embodiments apigenin-7-o-beta d-glucuronide is present in a composition useful according to the disclosure in any amount between about 0.05% and about 30% by weight based on the total weight of the composition, including all weight percents and ranges of weight percents therebetween. A *Hamelia patens* extract as provided in some embodiments contains aricine. In some embodiments aricene is present in a composition useful according to the disclosure in any amount between about 0.05% and about 30% by weight based on the total weight of the composition, including all weight percents and ranges of weight percents therebetween. A *Hamelia patens* extract as provided in some embodiments contains catequine. In some embodiments catequine is present in a composition useful according to the disclosure in any amount between about 0.05% and about 30% by weight based on the total weight of the composition, including all weight percents and ranges of weight percents therebetween. A *Hamelia patens* extract as provided in some embodiments contains 24-methylenecycloartane-3β-ol. In some embodiments 24-methylenecycloartane-3β-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains 24-methylcycloart-24-en-3β-ol. In some embodiments 24-methylcycloart-24-en-3β-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains 2 E-3,7,11,15,19-pentamethyl-2-eicosane-1-ol. In some embodiments 2 E-3,7,11,15,19-pentamethyl-2-eicosane-1-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains ephedrine. In some embodiments ephedrine is present in a composition useful according to the disclosure in any amount between about 0.05% and about 30% by weight based on the total weight of the composition, including all weight percents and ranges of weight percents therebetween. A *Hamelia patens* extract as provided in some embodiments contains flavonones. In some embodiments flavonones are present in a composition useful according to the disclosure in any amount between about 0.05% and about 30% by weight based on the total weight of the composition, including all weight percents and ranges of weight percents therebetween. A *Hamelia patens* extract as provided in some embodiments contains 2'-5-5'-7-tetrahydroxy-7-o-rutinoside. In some embodiments 2'-5-5'-7-tetrahydroxy-7-o-rutinoside is present in a composition useful according to the disclosure in any amount between about 0.05% and about 30% by weight based on the total weight of the composition, including all weight percents and ranges of weight percents therebetween. A *Hamelia patens* extract as provided in some embodiments contains 19-alpha-hydroxy asiatic acid. In some embodiments 19-alpha-hydroxy asiatic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains isomaruquine. In some embodiments isomaruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains isopteropodine. In some embodiments isopteropodine is present in a composition useful according to the disclosure in any amount between about 0.05% and about 30% by weight based on the total weight of the composition, including all weight percents and ranges of weight percents therebetween. A *Hamelia patens* extract as provided in some embodiments contains maruquine. In some embodiments maruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains the methyl ester of maruquine. In some embodiments the methyl ester of maruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains mitraphylline. In some embodiments mitraphylline is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin. In some embodiments narirutin is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin (2r). In some embodiments narirutin (2r) is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin (2s). In some embodiments narirutin (2s) is present in a composition useful according to the disclosure in any amount between about 0.05% and about 30% by weight based on the total weight of the composition, including all weight percents and ranges of weight percents therebetween. A *Hamelia patens* extract as provided in some embodiments contains oxindole alkaloids. In some embodiments oxindole alkaloids are present in a composition useful according to the disclosure in any amount between about 0.05% and about 30% by weight based on the total weight of the composition, including all weight percents and ranges of weight percents therebetween. A *Hamelia patens* extract as provided in some embodiments contains oxindole In some embodiments oxindole aricine is present in a composition useful according to the disclosure in any amount between about 0.05% and about 30% by weight based on the total weight of the composition, including all weight percents and ranges of weight percents therebetween. A *Hamelia patens* extract as provided in some embodiments contains palmirine. In some embodiments palmirine is present in a composition useful according to the disclosure in any amount between about 0.05% and about 30% by weight based on the total weight of the composition, including all weight percents and ranges of weight percents therebetween. A *Hamelia patens* extract as provided in some embodiments contains pigenin-7-o-beta D-glucuronide. In some embodiments pigenin-7-o-beta D-glucuronide is present in a composition useful according to the disclosure in any amount between about 0.05% and about 30% by weight based on the total weight of the composition, including all weight percents and ranges of weight percents therebetween. A *Hamelia patens* extract as provided in some embodiments contains pomolic acid. In some embodiments pomolic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains pteropodine. In some embodiments pteropodine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rumberine. In some embodiments rumberine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rosmarinic acid. In some embodiments rosmarinic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains rotundic acid. In some embodiments rotundic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains rumberine. In some embodiments rumberine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rutin. In some embodiments rutin is present in a composition useful according to the disclosure in any amount between about 0.05% and about 30% by weight based on the total weight of the composition, including all weight percents and ranges of weight percents therebetween. A *Hamelia patens* extract as provided in some embodiments contains seneciophylline. In some embodiments seneciophylline is present in a composition useful according to the disclosure in any amount between about 0.05% and about 30% by weight based on the total weight of the composition, including all weight percents and ranges of weight percents therebetween. A *Hamelia patens* extract as provided in some embodiments contains β-sitoster ol. In some embodiments β-sito sterol is present in a composition useful according to the disclosure in any amount between about 0.05% and about 30% by weight based on the total weight of the composition, including all weight percents and ranges of weight percents therebetween. A *Hamelia patens* extract as provided in some embodiments contains speciophylline. In some embodiments speciophylline is present in a composition useful according to the disclosure in any amount between about 0.05% and about 30% by weight based on the total weight of the composition, including all weight percents and ranges of weight percents therebetween.

A *Hamelia patens* extract as provided in some embodiments contains stigmast-4-en-3-3-dione. In some embodiments stigmast-4-en-3-3-dione is present in a composition useful according to the disclosure in any amount between about 0.05% and about 30% by weight based on the total weight of the composition, including all weight percents and ranges of weight percents therebetween. A *Hamelia patens* extract as provided in some embodiments contains stigmast-4-en-3-6-dione. In some embodiments stigmast-4-en-3-6-dione is present in a composition useful according to the disclosure in any amount between about 0.05% and about 30% by weight based on the total weight of the composition, including all weight percents and ranges of weight percents therebetween. A *Hamelia patens* extract as provided in some embodiments contains stigmasterol. In some embodiments stigmasterol is present in a composition useful according to the disclosure in any amount between about 0.05% and about 30% by weight based on the total weight of the composition, including all weight percents and ranges of weight percents therebetween. A *Hamelia patens* extract as provided in some embodiments contains tannins. In some embodiments tannins are present in a composition useful according to the disclosure in any amount between about 0.05% and about 30% by weight based on the total weight of the composition, including all weight percents and ranges of weight percents therebetween. A *Hamelia patens* extract as provided in some embodiments contains tormentic acid. In some embodiments tormentic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains uncarine F. In some embodiments uncarine F is present in a composition useful according to the disclosure in any amount between about 0.05% and about 30% by weight based on the total weight of the composition, including all weight percents and ranges of weight percents therebetween. A *Hamelia patens* extract as provided in some embodiments contains ursolic acid. In some embodiments ursolic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains 2-alpha-hydroxy ursolic acid. In some embodiments 2-alpha-hydroxy ursolic acid is present in a composition useful according to the disclosure in any amount between about 0.05% and about 30% by weight based on the total weight of the composition, including all weight percents and ranges of weight percents therebetween. The term "about" when used herein, such as in "about 30%", is to be understood as also including the exact numerical value occurring immediately subsequent to the word "about", in the same context. For example, the recitation of "about 30%" and "about 0.05%" includes the exact value specified, in this instance exactly 30% and exactly 0.05%, respectively. In some embodiments, each of the component materials in the listing above, when present in a *Hamelia patens* extract, are present in amounts within the above-specified ranges independently with respect to the amounts of the other component materials present.

As concerns any one or more than one of the foregoing materials in said listing which are described as being acids, the present disclosure includes the presence of such materials in their neutralized or anionic forms, and in alternate embodiments their esterified forms condensed with any alcohol or polyol selected. For those component compounds in the listing having a carboxylic acid function, the present disclosure includes the presence of such materials in their anionic forms, including without limitation their alkali metal salts, alkaline earth salts, ammonium salts and substituted ammonium salts, the concentration of the anionic forms of such material(s) being present in a composition according to the disclosure in the amounts specified for the acid form of the material(s). In some embodiments the concentration ranges for components present in a composition according to the disclosure are applied based on the weight percent of the anionic form of the material. In some embodiments, the concentration ranges in a composition according to the disclosure are determined based on the weight percent of the salt, including the cation present. Likewise when basic substances are recited, the present disclosure includes the presence of such materials in their protonated forms, the concentration ranges of such materials being present in a composition according to the disclosure in the amounts specified above for the basic form. In some embodiments the concentration ranges for a composition according to the disclosure is determined based on the weight percent of the protonated form of the material present. In some embodiments, the concentration ranges for a composition according to the disclosure is determined based on the weight percent of the protonated form of the material and including its anion present for charge neutrality.

In some embodiments, all of the materials in the above listing are present in a composition useful according to the disclosure. In other embodiments any one or more than one of the materials in the above listing are independently omitted from the contents of a composition useful according to the disclosure, such as by refining a *Hamelia patens* extract (including a crystalline *Hamelia patens* extract) for the purpose of removal of one, or any number greater than one, of component materials in the above listing present in the extract using techniques known to those skilled in the art. In other embodiments any one or any number greater than one of such components present in the listing may be purified using techniques known to those of ordinary skill in the art. For example, to remove nitrogenous bases the extract material is put up into aqueous solution and made alkaline, and extraction done using $CHCl_3$ to remove amino compounds, the aqueous layer being subsequently re-acidified or neutralized. In some embodiments, ammonia is used to make the material alkaline for purposes of such extraction, which ammonia is subsequently removed after the extraction having been completed by blowing with nitrogen or distilling or heating under reduced pressure. In other embodiments an aqueous extract of *Hamelia patens* is made slightly acidic by addition of HCl, and extractions are done using ethyl acetate, ether, chloroform, and/or hexanes. Following extraction, the aqueous layer is subjected to reduced pressure and slight heating or a sweep of nitrogen or other inert gas to facilitate removal of the HCl. In such embodiments, fractions obtained may be further treated to selectively separate or remove component materials present, using techniques known in the art including without limitation such techniques as preparatory chromatography columns, fractional distillation under vacuo, molecular distillation, precipitation and filtration, etc. In further embodiments, any one or more than one of any of the above-named components in the listing are produced synthetically or are otherwise acquired or produced, and are subsequently blended with one another to provide a blend that comprises a synthetic *Hamelia patens* extract that is useful according to the disclosure, such components that are selected to be present each being individually present at levels within the ranges specified herein based on the total weight of the topical medicament produced using *Hamelia patens* extract.

An extract of the plant *Hamelia patens* according to some embodiments of the disclosure may thus comprise a crude (water-based, H2O/alcohol based, oil-based, or petrolatum based) *Hamelia patens* extract from which any one, or any combination including any number more than one of, the component materials set forth in the listing above are omitted or removed from said extract, the resulting extract being useful according to this disclosure. In some embodiments at least any chosen two of the component materials selected from the group consisting of the materials recited in the listing above remain or are present in a *Hamelia patens* extract useful according to this disclosure, the component materials being independently present at concentrations within any of the ranges specified above in such compositions or extracts. In some embodiments at least any chosen three of the component materials selected from the group consisting of the materials recited in the listing above remain or are present in a *Hamelia patens* extract useful for providing a composition useful according to this disclosure, the component materials being independently present at concentrations within the ranges specified above in such compositions or extracts. In some embodiments at least any chosen four of the component materials selected from the group consisting of the materials recited in the listing above remain or are present in a *Hamelia patens* extract useful according to this disclosure, the component materials being independently present at concentrations within the ranges specified above in such composition or extracts. In some embodiments at least any chosen five of the component materials selected from the group consisting of the materials recited in the listing above remain or are present in a *Hamelia patens* extract useful according to this disclosure, the component materials each being independently present at any concentration within the ranges specified above in such compositions or extracts.

This disclosure includes the use of *Hamelia patens* extracts from which some of the components in the listing above have been removed, and also *Hamelia patens* extracts comprising a plurality of the materials in the listing above which are produced by combining previously-isolated purified component materials from such listing. In some embodiments, all alkaloids are omitted or removed when providing a *Hamelia patens* extract useful according to the disclosure, the remaining components of the listing remaining present. In some embodiments, all 2-alpha-hydroxyursolic acid is omitted or removed when providing a *Hamelia patens* extract useful according to the disclosure, the remaining components of the listing remaining present. In some embodiments, all flavonones are omitted or removed when providing a *Hamelia patens* extract according to the disclosure, the remaining components of the listing remaining present. In some embodiments, all apigenin-7-o-beta d-glucuronide is omitted or removed when providing a *Hamelia patens* extract useful according to the disclosure, the remaining components of the listing remaining present. In some embodiments, all aricine is omitted or removed when providing a *Hamelia patens* extract useful according to the disclosure, the remaining components of the listing remaining present. In some embodiments, all catequine is omitted or removed when providing a *Hamelia patens* extract useful according to the disclosure, the remaining components of the listing remaining present. In some embodiments, all flavonones is omitted or removed when providing a *Hamelia patens* extract useful according to the disclosure, the remaining components of the listing remaining present. In some embodiments, all 19-alphahydroxy Asiatic acid is omitted or removed when providing a *Hamelia patens* extract useful according to the disclosure, the remaining components of the listing remaining present. In some embodiments, all 24-methylenecycloartane-3β-ol is omitted or removed when providing a *Hamelia patens* extract useful according to the disclosure, the remaining components of the listing remaining present. In some embodiments, all 24-methylcycloart-24-en-3β-ol is omit ted or removed when providing a *Hamelia patens* extract useful according to the disclosure, the remaining components of the listing remaining present. In some embodiments, all 2 E-3,7,11,15,19-pentamethyl-2-eicosane-1-ol is omitted or removed when providing a *Hamelia patens* extract useful according to the disclosure, the remaining components of the listing remaining present. In some embodiments, all ephedrine is omitted or removed when providing a *Hamelia patens* extract useful according to the disclosure, the remaining components of the listing remaining present. In some embodiments, all 2'-5-5'-7-tetrahydroxy-7-o-rutinoside is omitted or removed when providing a *Hamelia patens* extract useful according to the disclosure, the remaining components of the listing remaining present. In some embodiments, all flavonones are omitted or removed when providing a *Hamelia patens* extract useful according to the disclosure, the remaining components of the listing remaining present. In some embodiments, all isomaruquine is omitted or removed when providing a *Hamelia patens* extract useful according to the disclosure, the remaining components of the listing remaining present. In some embodiments, all isopteropodine is omitted or removed when providing a *Hamelia patens* extract useful according to the disclosure, the remaining components of the listing remaining present. In some embodiments, all maruquine is omitted or removed when providing a *Hamelia patens* extract useful according to the disclosure, the remaining components of the listing remaining present. In some embodiments, all the methyl ester of maruquine is omitted or removed when providing a *Hamelia patens* extract useful according to the disclosure, the remaining components of the listing remaining present. In some embodiments, all mitraphylline is omitted or removed when providing a *Hamelia patens* extract according to the disclosure, the remaining components of the listing remaining present. In some embodiments, all narirutin is omitted or removed when providing a *Hamelia patens* extract useful according to the disclosure, the remaining components of the listing remaining present. In some embodiments, all narirutin (2r) is omitted or removed when providing a *Hamelia patens* extract useful according to the disclosure, the remaining components of the listing remaining present. In some embodiments, all narirutin (2s) is omitted or removed when providing a *Hamelia patens* extract useful according to the disclosure, the remaining components of the listing remaining present. In some embodiments, all oxindole alkaloids are omitted or removed when providing a *Hamelia patens* extract useful according to the disclosure, the remaining components of the listing remaining present. In some embodiments, all oxindole aricine is omitted or removed when providing a *Hamelia patens* extract useful according to the disclosure, the remaining components of the listing remaining present. In some embodiments, all palmirine is omitted or removed when providing a *Hamelia patens* extract useful according to the disclosure, the remaining components of the listing remaining present. In some embodiments, all pigenin-7-o-beta D-glucuronide is omitted or removed when providing a *Hamelia patens* extract useful according to the disclosure, the remaining components of the listing remaining present. In some embodiments, all pomolic acid is omitted or removed when providing a *Hamelia patens* extract useful according to the disclosure, the remaining components of the listing remaining present. In some embodiments, all pteropodine is omitted or removed when providing a *Hamelia patens* extract useful according to the disclosure, the remaining components of the listing remaining present. In some embodiments, all rumberine is omitted or removed when providing a *Hamelia patens* extract useful according to the disclosure, the remaining components of the listing remaining present. In some embodiments, all rosmarinic acid is omitted or removed when providing a *Hamelia patens* extract useful according to the disclosure, the remaining components of the listing remaining present. In some embodiments, all rotundic acid is omitted or removed when providing a *Hamelia patens* extract useful according to the disclosure, the remaining components of the listing remaining present. In some embodiments, all rutin is omitted or removed when providing a *Hamelia patens* extract useful according to the disclosure, the remaining components of the listing remaining present. In some embodiments, all seneciophylline is omitted or removed when providing a *Hamelia patens* extract useful according to the disclosure, the remaining components of the listing remaining present. In some embodiments, all β-sitos terol is omitted or removed when providing a *Hamelia patens* extract useful according to the disclosure, the remaining components of the listing remaining present. In some embodiments, all speciophylline is omitted or removed when providing a *Hamelia patens* extract useful according to the disclosure, the remaining components of the listing remaining present. In some embodiments, all stigmast-4-en-3-3-dione is omitted or removed when providing a *Hamelia patens* extract useful according to the disclosure, the remaining components of the listing remaining present. In some embodiments, all stigmast-4-en-3-6-dione is omitted or removed when providing a *Hamelia patens* extract useful according to the disclosure, the remaining components of the listing remaining present. In some embodiments, all stigmasterol is omitted or removed when providing a *Hamelia patens* extract useful according to the disclosure, the remaining components of the listing remaining present. In some embodiments, all tannins are omitted or removed when providing a *Hamelia patens* extract useful according to the disclosure, the remaining components of the listing remaining present. In some embodiments, all tormentic acid is omitted or removed when providing a *Hamelia patens* extract useful according to the disclosure, the remaining components of the listing remaining present. In some embodiments, all uncarine F is omitted or removed when providing a *Hamelia patens* extract useful according to the disclosure, the remaining components of the listing remaining present. In some embodiments, all ursolic acid is omitted or removed when providing a *Hamelia patens* extract useful according to the disclosure, the remaining components of the listing remaining present. As a non-limiting example, in some embodiments, all flavones, all rutin, and ephedrine are removed or omitted, the remaining components of the listing remaining present in a *Hamelia patens* extract useful according to this disclosure; however, any one or combination including more than one material in the listing may be removed or omitted. A combination, including a *Hamelia patens* extract, according to the disclosure and useful in accordance with providing compositions according to some embodiments of this disclosure may thus contain any number between about one and about all of the foregoing materials in the listing, in any combination, each, when present, being independently present in any amount within the ranges specified above.

For some embodiments of the disclosure the *Hamelia patens* extract is present in combination with other materials, of which petrolatum is one non-limiting example. In some embodiments a *Hamelia patens* extract (including those described above which omit one or more than one materials from said listing) is present as a component of a mixture comprising a dermatologically-acceptable carrier, which in some embodiments comprises a lotion, skin crème, ointment, or salve. For these embodiments, the term "dermatologically-acceptable carrier" is used in its ordinary sense relative to the different embodiments herein, generally including dermatologically-acceptable, non-toxic diluents or vehicles useful in formulation of dermatological compositions for topical application to human skin. The term "serum" as used herein can mean any composition comprising *Hamelia patens* extract in combination with a dermatologically-acceptable carrier, regardless of the concentration of *Hamelia patens* extract present in such composition.

Dermatologically-acceptable carriers can include, without limitation, one or more than one material selected from the group consisting of buffering agents, solubilizing agents, stabilizing agents, liquids such as water, saline solution, glycerol and ethanol. Such carriers enable a dermatologically-acceptable composition to be formulated as liquids, gels, syrups, slurries, suspensions, emulsions, salves, crèmes, ointments and the like for topical application to human skin to induce formation of granulation tissue in, on, or at the location of a third-degree burn wound present. A discussion of analogous pharmaceutically-acceptable carriers is available in Remington's Pharmaceutical Sciences (Mack Pub. Co., N.J. 1991), the general idea being the same insomuch as the topical medicament composition that is to be topically applied to human skin according to this disclosure does not cause any deleterious effects to the subject's skin and acts as a carrier for the *Hamelia patens* extract it contains.

Dermatologically-acceptable carriers include any and all compositions capable of functioning as carriers for *Hamelia patens* extract intended for topical application to human epidermal tissue ("skin") or skin areas having third-degree burns for inducing formation of granulation tissue in, on, or at the location of a third-degree burn wound present, without undue toxicity, incompatibility, instability, allergic response, etc. Numerous examples of ingredients useful in providing dermatologically-acceptable carriers and compositions having dermatologically-acceptable carriers for delivering active agents to the skin are well-known in the art and include without limitation those disclosed in U.S. Pat. Nos. 5,709,868; 4,992,478; 4,820,508; 4,608,392; and 4,559,157, which are incorporated herein by reference thereto. Topical application and words of similar import used herein mean to apply or spread a composition onto the surface of skin. A topical medicament is a composition that is formulated to be administered to skin by topical application. Within the class of dermatologically-acceptable carriers are included water, water-based carriers, alcohols, alcohol-based carriers, oils, and oil-based carriers, mineral oil and petrolatum-based carriers chosen for their ability to dissolve or disperse components present in the *Hamelia patens* extract.

As used herein, "topical composition" means any composition containing an extract of *Hamelia patens* in combination with a dermatologically-acceptable carrier and any other optionally added ingredients known to be used or useful in compositions intended and suitable for application to human skin or skin areas which have experienced a third-degree burn with no adverse skin reactions occurring. Topical compositions useful in carrying out a method of this invention can include various materials, including moisturizers, anti-oxidants, humectants, defoliants, oils, waxes, emulsions, emulsifiers, chelating agents, buffering agents, preservatives, and various cosmetics.

Topical application of *Hamelia patens* extract is accomplished in some embodiments by providing a combination of *Hamelia patens* extract with a dermatologically-acceptable carrier in which compounds present in the *Hamelia patens* extract are soluble per se, or are effectively solubilized (e.g., as a solution, suspension, emulsion, or microemulsion), and contacting or applying such combinations to human skin or skin which has experienced a third-degree burn.

In some embodiments, relatively low concentrations of *Hamelia patens* extract or any of its selected components in a combination according to the disclosure may be employed for instances in which more frequent topical application to human skin is undertaken, as compared to the frequency of application to human skin of a composition according to the disclosure in which the *Hamelia patens* extract is present at a higher concentrations. In some embodiments a topical medicament composition comprising *Hamelia patens* extract in combination with a dermatologically-acceptable carrier is formulated to contain at least about 0.25% and up to about 25% by weight based on the total weight of the composition of *Hamelia patens* extract, and accordingly suitable carriers can be readily chosen which can solubilize or disperse the components of the *Hamelia patens* extract at such concentrations. In some embodiments, *Hamelia patens* extract is present in a topical composition according to the disclosure in any amount between about 0.01% to about 30% by weight based on the total weight of the topical composition, including all percentages and ranges of percentages therebetween. In some embodiments a topical composition according to the disclosure contains about 10% by weight total *Hamelia patens* extract.

While the carrier for extract of *Hamelia patens* can consist of or comprise a relatively simple solvent or dispersant such as oils, the carrier may comprise materials which aid in percutaneous delivery and penetration of one or more than one of the components of a *Hamelia patens* extract into dermal lipid layers. Many of such compositions are well-known in the art of transdermal drug administration, and can take the form of lotions, creams, ointments, salves, gels and solid compositions (e.g., stick-form preparations). Some typical compositions include lotions containing water and/or alcohols and emollients such as hydrocarbon oils and waxes, silicone oils, hyaluronic acid, vegetable, animal, marine, or marine animal fats or oils, glyceride derivatives, fatty acids or fatty acid esters or alcohols or alcohol ethers, lanolin and derivatives, polyhydric alcohols or esters, wax esters, sterols, phospholipids and other materials having like function, and also emulsifiers (nonionic, cationic or anionic), although some of the emollients inherently possess emulsifying properties. These same general ingredients can be formulated into a crème, a lotion, gels, or solid sticks by utilization of different proportions of the ingredients and/or by inclusion of thickening agents such as gums or other forms of hydrophilic particles or colloids. Such compositions are within the class of those comprising dermatologically-acceptable carriers. In some embodiments those most preferred for topical application to human skin are carriers which are fat-soluble, i.e., those which can penetrate human dermal layers or fluids present, and deliver components of *Hamelia patens* extract to the body to induce formation of granulation tissue in, on, or at the location of a third-degree burn wound present. In alternate embodiments, a *Hamelia patens* extract according to the disclosure may be applied to human skin using a time-release patch, as are used in hormone delivery, nicotine patches, anti-acne patches, and the like. Crèmes, aqueous solutions, pastes, powders, etc. are all suitable delivery vehicles for an extract of *Hamelia patens* or one or more of its components to human skin.

Thus, a *Hamelia patens* extract of the present disclosure (which term includes crystalline and other extracts mentioned herein, synthetically-assembled or otherwise provided), and alternately any of its components in any number, combination, and quantity as earlier set forth may be present in a wide range of compositions suitable to be applied to human skin. In addition, a *Hamelia patens* extract according to the present disclosure may be present in combination with surfactants and materials which are conventionally recognized as being used in skin care products, in which the concentration of *Hamelia patens* extract ranges from about 1% to up to about 60% by weight based on the total weight of the composition, including all percentages and ranges of percentages therebetween.

Surfactants and other materials which can be used in combination with a *Hamelia patens* extract in forming topical compositions useful for inducing formation of granulation tissue in, on, or at the location of a third-degree burn wound present on the skin include without limitation: amphoteric/zwitterionic surfactants; anionic surfactants; nonionic surfactants; cationic surfactants; and optional ingredients, including without limitation those described below.

Amphoteric surfactants suitable for inclusion in a topical composition according to this disclosure comprising a *Hamelia patens* extract or any one or more than one of its components independently present in any amount within the ranges specified above can broadly be described as surface active agents containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants suitable for inclusion in a composition according to this disclosure comprising a *Hamelia patens* extract or any of its components independently present in any amount specified in the ranges above can be described as surface active agents having a positive and negative charge in the same molecule which molecule is zwitterionic at all pH's. Zwitterionic surfactants are exemplified by betaines and sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of amphoteric and zwitterionic surfactants suitable for inclusion in a composition comprising a *Hamelia patens* extract or any of its components independently in any amount specified within the ranges above according to the present disclosure include the alkali metal, alkaline earth metal, ammonium or substituted ammonium salts of alkyl amphocarboxyglycinates and alkylamphocarboxypropionates, alkyl amphodipropionates, alkyl monoacetate, alkyl diacetates, alkylamphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Anionic surfactants suitable for inclusion in a composition comprising a *Hamelia patens* extract or any of its components independently present in any amount specified in the ranges above according to the present disclosure are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants. Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water-soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants include alkylsulfosuccinates, alkyl ethersulfosuccinates, olefin sulfonates, alkyl sarcosinates, alkyl monoglyceride sulfates and ether sulfates, alkyl ether carboxylates, paraffinic sulfonates, mono and di-alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or propylene oxide (PO), preferably EO. Specific anionic surfactants which may be selected include linear alkyl benzene sulfonates, including without limitation those such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

Nonionic surfactants may also be present in a composition according to the disclosure comprising a *Hamelia patens* extract or any of its components independently present in any amount specified within the ranges above. The nonionic surfactant(s) may be any of the known nonionic surfactants which, as with other surfactants discussed herein, are generally selected on the basis of compatibility, effectiveness, and economy, and present in a composition according to the disclosure in effective amount to enhance wettability or permeability of human skin when topically applied thereto or to otherwise beneficially modify activity of components present in a combination provided herein. Examples of useful nonionic surfactants include without limitation condensates of ethylene oxide with a hydrophobic moiety which has an average hydrophilic lipolytic balance (HLB) between about 8 to about 16, and in some embodiments between about 10 and about 13. Non-ionic surfactants include the ethoxylated primary or secondary aliphatic alcohols having from about 8 to about 24 carbon atoms, in either straight or branch chain configuration, with from about 2 to about 40, and in some embodiments between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide.

Many cationic surfactants are known in the art and almost any cationic surfactant having at least one long chain alkyl group of about 10 to 24 carbon atoms is suitable for optional use as a component in a composition comprising a *Hamelia patens* extract according to the present disclosure.

Other optional ingredients or additives which may be used in combination with *Hamelia patens* extract in formulating compositions according to the present disclosure include pH adjusting chemicals, for example, loweralkanolamines such as monoethanolamine (MEA) and triethanolamine (TEA). Sodium hydroxide solutions may also be utilized as an alkaline pH adjusting agent, as well as any organic acids, mineral acids or other acids known for their ability to adjust pH. The pH adjusting chemicals function to neutralize acidic or basic materials that may be present. Mixtures of more than one pH adjusting chemical can also be utilized, as well as buffers.

Phase regulants are well known and may also be optionally present in a composition of the disclosure. These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Other optional supplemental additives include stabilizing agents, antioxidants, uv-light inhibitors or absorbers, preservatives, buffers formulated to be at any selected pH level within 0.5 pH units of normal skin, polyacids, anti-biotics, and bacteriacides.

*Hamelia patens* extracts of the present disclosure are useful in providing compositions which contain materials typically known to and used by those skilled in the art of formulation as being useful in formulating skin-care compositions, shampoos and other products intended for topical application. For purposes of this disclosure, the words "materials typically known to and used by those skilled in the art of formulation" means one, or any combination comprising more than one of the materials selected from the group consisting of: fatty acids, alkyl sulfates, ethanolamines, amine oxides, alkali carbonates, water, ethanol, isopropanol, pine oil, sodium chloride, sodium silicate, polymers, alcohol alkoxylates, zeolites, aloe, vitamins, emu oil, anti-oxidants, carotenoids, terpenoids, flavonoids, hormones, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonate diphenyl oxide, and water soluble alkylbenzene sulfonates or alkyltoluene sulfonates, each present when selected in conventionally-used amounts to achieve their conventional function.

In some embodiments, a *Hamelia patens* extract of the present disclosure may comprise a fatty acid soap together with other non-soap surfactants, such as mild synthetic surfactants. Moisturizers and/or emollients and polymeric skin feel and mildness aids including dimethicone can also be selected to be present. The compositions may further optionally include thickeners (e.g., magnesium aluminum silicate, CARBOPOL® polymers), conditioners, water soluble polymers (e.g., carboxymethyl cellulose), dyes, perfumes, and germicides.

In some embodiments, a salve, crème, ointment, emulsion, or lotion containing an extract of *Hamelia patens* according to the disclosure is applied topically to human skin which has experienced a third-degree burn, with like gentle application as one would employ if using any other topical medicament to a third-degree burn. In some embodiments, a salve, crème, ointment, or lotion including a *Hamelia patens* extract according to the disclosure is applied once daily to such an area of the body where a third-degree burn is present. In other embodiments, a salve, crème, ointment, or lotion including a *Hamelia patens* extract according to the disclosure is applied twice daily to a skin area which has experienced a third-degree burn. In other embodiments, a salve, crème, ointment, or lotion including a *Hamelia patens* extract according to the disclosure is applied thrice daily to a skin area which has experienced a third-degree burn. In other embodiments, a salve, crème, ointment, or lotion including a *Hamelia patens* extract according to the disclosure is applied four times daily to a skin area which has experienced a third-degree burn. In other embodiments, a salve, crème, ointment, or lotion including a *Hamelia patens* extract according to the disclosure is applied more than four times daily, on an as-needed or as-desired basis to a skin area which has experienced a third-degree burn. The foregoing treatment frequencies can be used with any topical composition containing *Hamelia patens* extract having the *Hamelia patens* extract present at any concentration level within the percentage ranges specified herein. In general, a single daily application has efficacy for catalyzing formation of granulation tissue in a third-degree burn, while three times daily application is expected to work well in nearly all cases. In some embodiments, application more than four times daily provides no further benefit than does the four times daily application.

*Hamelia patens* extracts as provided herein, whether present in crystalline, amorphous, gummy or liquid form, including oil-based liquids, aqueous liquids or alcohol-water mixtures, and topical compositions, as described, are useful in combination with liposomes in a topical composition. Suitable liposomes include those recognized by those skilled in the art as being useful in combination with plant-derived extracts and components present therein as herein described to enhance delivery of such extracts or components into the dermal layers of a human subject. Liposomes include artificial microscopic vesicles consisting of an aqueous core present and enclosed within either one, or a plurality of phospholipid layers, which structured materials are useful to convey one or any combination including any number greater than one components present in *Hamelia patens* extract through the dermal layers when a composition of this disclosure includes liposomes in an effective amount.

*Hamelia patens* extracts as provided herein, whether present in crystalline form or liquid form, including oil-based liquids, aqueous liquids or alcohol-water mixtures, and topical compositions, as described, are useful in combination with nanoparticles in a topical composition. As used herein, a nanoparticle is any particulate form that is less than about one micrometer in at least one dimension, including particulate forms that are less than one micrometer in at least one dimension. Suitable nanoparticles include those recognized by those skilled in the art as being useful in combination with plant extracts and materials present in plant-derived extracts, and include without limitation such nanoparticles as: solid core nanoparticles, hollow core nanoparticles, lipid nanoparticles, polyethylene glycol ("PEG") nanoparticles, chitosan nanoparticles.

Below are set forth several examples of materials and methods useful in carrying out non-limiting exemplary embodiments of the invention. These examples are intended to be interpreted as being exemplary of various embodiments of this disclosure for understanding by physicians and not delimitive thereof, as physicians being those of ordinary skill in the art to whom this specification is directed for the most part, readily appreciates.

Example I

Petrolatum Extract of *Hamelia patens*

A one-liter volume of cut and cleaned leaves of *Hamelia patens* are compressed and combined with about 125 ml of petrolatum, the mixture being heated to about 65 degrees Centigrade for about 10 minutes. The leafy material is mechanically separated from the petrolatum, which is optionally filtered, to afford a petrolatum-borne extract of the plant *Hamelia patens*.

Example II

Aqueous Alcohol Extract of *Hamelia patens*

500 grams of ground *Hamelia patens* leaves are combined with 500 ml of a solvent mixture that contains 10% by volume of ethanol in water. The liquid is maintained at room temperature for 30 minutes with occasional stirring of the leaves and solvent. The resulting solution is centrifuged to remove solids and filtered to provide a liquid extract of *Hamelia patens* in solution.

Example III

Crystalline Extract of *Hamelia patens*

The liquid extract provided in Example II is placed in a vacuum still, heated to fifty degrees Centigrade, and subjected to reduced pressure of 300 torr with a slow sweep of nitrogen gas being admitted over the liquid to enhance removal of solvent, the pressure being maintained at 300 torr. Once the solvent has been removed, a crystalline extract of *Hamelia patens* remains. This extract is optionally purified via re-crystallization using an ethanol-water mixture.

Example IV

Topical Skin Lotion

Ten grams of re-crystallized crystalline extract provided in Example III were placed in a 150 ml beaker. Ninety five grams of Vaseline® moisture locking lotion (unfragranced) were subsequently added to the beaker, and the contents mixed by mechanical means until the extract was substantially evenly dispersed within the lotion to provide a lotion containing 10% of an extract of the plant *Hamelia patens*. The concentration of *Hamelia patens* extract in the lotion is optionally adjusted to any desired level less than 10% by addition of any selected further quantity of the neat lotion, with subsequent mechanical mixing until homogeneous.

Example V

Vitamin-Fortified Lotion

Forty five grams of the 10% lotion of example IV is placed in a 100 ml beaker and five grams of Vitamin E oil are added and the beaker contents mixed until at least substantially uniform to provide a Vitamin-fortified lotion.

Example VI

Lotion Concentrate

Fifty grams of recrystallized crystalline extract provided in Example III were placed in a 150 ml beaker. Fifty grams of VASELINE® moisture locking lotion (unfragranced) were subsequently added to the beaker, and the contents mixed by mechanical means until the extract was substantially evenly dispersed within the lotion to provide a lotion containing 50% of an extract of the plant *Hamelia patens*. This lotion may be used as a lotion concentrate suitable as a base stock from which other lotions may be produced, such as by simple dilution to any desired concentration.

Example VII

Salve Containing *Hamelia patens*

To 95 grams of a petrolatum-based extract of the plant *Hamelia patens* prepared according to example I, are added five grams of DMSO and 0.5 grams of soy lecithin. The mixture is blended until at least substantially uniform to provide a salve having enhanced transdermal mobility.

Example VIII

Oil in Water Emulsion

The following ingredients are blended together:

| | |
|---|---|
| fatty alcohols (50/50 mix C16 + C18) | 15 grams |
| mineral oil | 10 grams |
| petrolatum | 3 grams |
| PEG-15 (oleyl.cetyl alc.) | 5 grams |
| water | 67 grams |
| crystalline extract from example III | 7.5 grams |

The emulsion formed from combining the above materials is one non-limiting example of a serum that can be applied directly to human skin for inducing formation of islands of granulation tissue in a third-degree burn present on the skin of the subject individual.

Example IX

A topical composition described in Example IV, is modified to contain 5% of *Hamelia patens* extract by addition of further neat lotion. The 5% *Hamelia patens* lotion is suitable to be topically applied to third-degree burn wounds on the skin of a human subject.

Example X

A topical composition described in Example IV, modified to contain 3% of *Hamelia patens* extract by addition of further neat lotion. The 3% *Hamelia patens* lotion is suitable to be topically applied to third-degree burn wounds on the skin of a human subject.

Example XI

A topical composition described in Example IV, modified to contain 1% of *Hamelia patens* extract by addition of further neat lotion. The 1% *Hamelia patens* lotion is suitable to be topically applied to third-degree burn wounds on the skin of a human subject.

Example XII

A topical composition described in Example IV, is modified to contain 15% of *Hamelia patens* extract by addition of crystalline *Hamelia patens* extract. The 15% *Hamelia patens* lotion is suitable to be topically applied to third-degree burn wounds on the skin of a human subject.

Provided below is a case study of the use of a skin serum comprising *Hamelia patens* extract in a dermatologically-acceptable carrier. The exact composition o the carrier is generally not a critical factor, as the *Hamelia patens* extract is the active ingredient. As mentioned previously however, some carrier compositions can increase the efficacy of the *Hamelia patens* extract by promoting its absorption into tissues onto which the topical serum is applied.

Example XIII—Case Study

A Caucasian male aged thirteen years was holding a fuel can near a controlled brush fire, when fire was communicated to the fuel can, causing its explosion and totally engulfing the boy in flames. Witnesses extinguished the flames, and the patient was life-flighted to the Burn Unit at Parkland Hospital in Dallas, Tex. The diagnosis was third degree burns over ninety percent (90%) of the patients' body. He was intubated, received tracheostomy, and spent 9 months in the Parkland Burn Unit ICU on his first hospitalization, during which he suffered cardiac arrest on three separate occasions. Four months were spent in the Rehabilitation Center afterwards. After being hospitalized for over a year, he did follow-ups three (3) times a week as an out-patient for PT and OT. In total, this young man underwent over thirty (30) surgeries for scar revisions, skin grafts, wound care, tracheostomy, scar release, and wound care.

The patient had insufficient normal skin to be harvested for use in skin grafts, and it was necessary to grow grafts from his DNA using small swatches of his normal skin. He received many months of antibiotic therapy because of numerous persistent infections over his body—*Pseudomonas aeruginosa, Staphylococcus aureus*, and *Streptococcus*, which resulted in a large number of draining wounds over his entire body that simply would not heal. The patient was dismissed to go home with many areas of delayed wound healing on his back and both legs, featuring large open eschar wounds due to escharectomy procedures on his back and both legs. These wounds included persistent open, draining sores on both sides of his back that had failed to heal over a three-year time span.

A skin serum containing 10% by weight of *Hamelia patens* extract was topically applied to the wounds on his back one time daily, while under the care and watchful eye of his physician. As a direct result of topical application of the *Hamelia patens* extract, all of the wounds on the patients' back closed within a time span of several days to five weeks after initial topical application of the *Hamelia*

*patens* serum, and remained closed. The person of ordinary skill at this point immediately recognizes the major advance this invention represents in all the history of known medicine for humans in inducing granulation tissue in third-degree burns.

The patient subsequently was admitted for surgical excision of multiple large keloid contractures of both popliteal fossae and primary split-thickness skin grafts (STSG), and for debridement of the sloughed STSG wounds. Surgical excision of keloid contracted scars on the posterior aspect of both knees and lower legs was performed, and skin grafts were applied. All of these grafts failed to take. The supervising surgeon determined that yet another surgery would be necessary to attempt further skin grafts.

Sixteen days after STSG excision of the knees and legs, a skin serum containing 10% of *Hamelia patens* extract was topically applied to these areas one time per day. Within 48 hours of the first application of the 10% *Hamelia patens* skin serum to these areas, active islands of granulation tissue were visually observed in the wounds. Surprisingly, the wounds on the patients' legs showed visually-observable and unexpected and amazing rapid development of further islands of granulation tissue without keloid formation or sepsis, over a period of only 4 days. Again at this point, the person of ordinary skill in the art immediately recognizes the major advance this represents in the history of recorded medicine. These applications of *Hamelia patens* extract were applied to the third-degree burns on the subjects' knees and legs in the fifth year after the initial fuel can explosion. When the patient subsequently returned for a follow-up checkup after four days of having the 10% *Hamelia patens* skin serum applied to his wounds one time daily, the surgeon showed much surprise and delight and stated, "I don't know what you are using on these wounds, but keep using it." The large open third-degree burns on both wounds had 90% coverage by granulation tissue after only four days of application of the 10% *Hamelia patens* extract serum. This is a remarkable result never before seen in all of recorded medicine, and those of ordinary skill in the art immediately recognize the major advance provided by the present invention for persons having experienced third-degree burns, which previously have been recognized as requiring skin grafts.

Ten days after initial topical application of the 10% *Hamelia patens* extract serum, the leg wounds were 100% covered, totally closed over. No side effects were observed and no further incidences of wound sepsis remained. The surface of wound granulation grew flat and without any neuropathy. All surgical areas were seen to be completely healed within several weeks, with no infections, no sepsis, and no keloid formation. All scars were flat and smooth. No recurrences of wound dehiscence were observed following this topical treatment.

At the time of the filing of the instant Application for Patent, the patient is completely independent and living a normal life, having ridden in a rodeo in December 2016. The attendant registered nurse reports that with the healing of the patients' back and legs wounds, he is now able to participate in swimming, beach events, and other sport/social events with his peers without fear of embarrassment due to drainage or infection.

Granulation tissue is new connective tissue and tiny blood vessels which form on the surfaces of a wound during the healing process. It is recognized in the medical arts that granulation tissue grows from the base of a given wound. In the present invention, the formation of granulation tissue is induced to occur within the periphery of a third-degree wound, that is—away from the peripheral edges of the wound, which is in the interior of the surface area of the wound, away from the periphery, which is an unexpected result since burn wounds are seen to only heal from the periphery. Clearly, some previously-unknown mechanism is at work here. However, formation of granulation tissue was also observed to have been induced to occur simultaneously at the periphery of the wound as well. Granulation tissue can be properly defined as new living mysenchymal tissue, and is described in the article: *Granulation Tissue* by Geoffrey Hadfield, MD in Ann. Royal Coll. Surg. December 1951 9(6): pp. 397-407, which is herein incorporated by reference.

The present invention is significant in part because topical application of an ointment, salve, lotion, serum, etc. containing *Hamelia patens* extract has been found to surprisingly induce formation of granulation tissue in open third-degree burn wounds, with amazing rapidly. This is true for even third-degree burn wounds which failed to heal over at least a four year time span under modern medical supervision. Moreover, it is striking that such formation of granulation tissue is visibly observable within 48 hours of initial topical application of a skin serum, etc., when it contains about 10% by weight of *Hamelia patens* extract as provided herein. Workers in the field of treating burn victims are licensed physicians having a high level of skill, and at present, other than the instant invention, they recognize that there is nothing known to mankind that can be topically applied to a third-degree burn on the skin, which causes granulation tissue to form. This is especially important due to the well known nature of the healing process described in the background section of this specification, relating to the healing mechanisms of first-degree skin burns and second-degree skin burns. In the case of third degree skin burns, there are no hair follicles or sweat glands surviving from which healing can occur, and it has always been believed in the past that healing must originate in the cases of third-degree burns from areas peripheral to the wound itself. It is thus truly remarkable that topically-applied *Hamelia patens* extract can induce or cause granulation tissue to occur in the middle of a burn wound, away from the periphery of the wound. Since granulation tissue is known to grow from the base of a wound, and in the case of third-degree burns the body is damaged deeply through all of the dermis, there is no base from which granulation tissue could grow, in the conventional sense. Such a result is not documented in all of medicine, to date and the present invention accordingly represents a significant advance in this art.

Although some methods of the present invention have been described in some embodiments as employing skin crème, lotion, salve, gel or other dermatologically-acceptable carrier containing *Hamelia patens* extract at a concentration of 10% by weight, other concentrations of *Hamelia patens* extract in a skin crème, lotion, salve, gel or other dermatologically-acceptable carrier are suitable for use according to this invention to achieve like results. Without limitation, any topical composition comprising a dermatologically-acceptable carrier in combination with *Hamelia patens* extract wherein the concentration of *Hamelia patens* extract in the topical composition is any concentration in the range of between 1.0% and 30.0%, including all percentages and ranges of percentages therebetween, is sufficient for inducing formation of granulation tissue in third-degree burns on the skin of humans or other mammals within a fortnight and in some embodiments within 48 hours following its topical application to a third-degree burn. In some embodiments, any concentration of *Hamelia patens* extract in a dermatologically-acceptable carrier in the range of between 5.0% and 15.0%, including all percentages and ranges of percentages therebetween, are sufficient for rapidly inducing the formation of granulation tissue in a third-degree wound on the skin of a human subject. However, concentrations of *Hamelia patens* extract in a topical medicament of this disclosure greater than 15% or 30% can be employed up to the practical limit of usage, which is about 50% by weight of the composition. The concentration of 10% appears to be very efficacious.

After reading this specification, one of ordinary skill recognizes that various application regimens for a topical composition described herein are possible. After reading this Specification, the person of ordinary skill in the art immediately recognizes that it is a matter of routine experimentation to apply a topical composition containing *Hamelia patens* extract in combination with a dermatologically-acceptable carrier any number of times per day as desired, and using any selected concentration of *Hamelia patens* extract stated herein in a topical composition. According to some embodiments, a topical composition comprising *Hamelia patens* extract in combination with a dermatologically-acceptable carrier having any amount of *Hamelia patens* extract present between 1% and 20% by weight of the topical composition, including all percentages and ranges of percentages therebetween, can be applied to human skin for inducing formation of granulation tissue in or on a third-degree burn on any skin area of a human subject. This can be once daily, twice daily, three times daily, four times daily, five times daily and six times daily, as frequently as desired at the discretion of the physician or patient. In some embodiments, a topical medicament containing *Hamelia patens* extract is applied to a third-degree burn at least twice per day. In other embodiments, a topical medicament containing *Hamelia patens* extract is applied to a third-degree burn at least three times per day. In other embodiments, a topical medicament containing *Hamelia patens* extract is applied to a third-degree burn at least four times per day. While in some embodiments, a single application of a topical composition containing 10% by weight of *Hamelia patens* extract is sufficient to induce formulation of granulation tissue in or on a third-degree burn wound within 48 hours, and even within 24 hours, in most cases the compositions described can be applied more often, desirably at the time of changing the patients' wound dressing(s). Applying the composition having any selected amount between 2% by weight of *Hamelia patens* extract and 25% by weight of *Hamelia patens* extract once per day, twice per day, three times per day, four times per day, or more frequently, for any time period of from one to 30 days are included within the realm of effective amounts and frequencies for inducing granulation tissue on a third-degree burn wound according to the invention. It is well within the skill level of the physicians who are persons of ordinary skill in this art to determine using only routine experimentation, what an effective amount and frequency are for inducing granulation tissue, since granulation tissue can be seen, and since applying a topical composition is a simple act which even children routinely perform using sun tan lotions. The physician or attendant needs only apply a topical composition provided herein, and observe the patients' wounds to visibly see the granulation tissue.

It is convenient to apply a *Hamelia patens* skin serum to a third-degree burn at the time of changing the wound dressing that has been applied to a wound. As is known, third-degree wounds are covered from air exposure during their healing by conventional wound dressings, which often include the use of gauze. Wound dressings require being changed at least daily and often two, three or four times daily, depending on the specific facts of each case, response of the patient's body, etc. At the time of changing a wound dressing, the old dressing material is removed and the wound may be cleaned of extraneous matter prior to applying an ointment and then dressing the wound with gauze or other dressings. In some embodiments, a *Hamelia patens* extract skin serum is applied to a third-degree wound after it has been cleaned and prior to dressing the wound with gauze. In this sense, the present invention provides novel wound dressing composition for third-degree skin burns. It is an inherent part of the claimed invention, that prior to inducing granulation tissue formation in a third degree burn wound, that a subject having a third-degree burn is present or provided.

Methods according to the present disclosure have been found to be particularly efficacious for inducing formation of granulation tissue (including islands thereof) on chronic, un-healing, large-sized, post-escharotomy burn wounds which are colonized with bacterium. These types of wounds are sometimes recognized in the art as being essentially un-healable, even after multiple attempts at skin grafts, wherein the attempted grafts unfortunately, slough-off, or do not "take" to the patient's skin or body, and automatically at some time fall off the wound. Treatment methods provided herein when topically applied over an entire escharotomy sites were found to stimulate autogenous granulation tissue in the middle of the wound surfaces, covering the wound surface completely. Shortly thereafter, autogenous epithelialization followed, to complete total wound new skin coverage without the need for skin grafting and without keloid scar formation. Antibiotic medications may be stopped thereafter. As used herein, chronic has its normal art-recognized meaning, including without limitation burn wounds that do not heal after one month's time.

Although this invention has been described and disclosed in relation to various embodiments, modifications, combinations, and alterations of the features of various embodiments disclosed become apparent to persons of ordinary skill in this art after reading and understanding the teachings of this specification and the claims appended hereto in view of the knowledge of one skilled in the art. The present disclosure includes subject matter defined by any combinations of any one (or more) of the features, elements, or aspects present described in reference to any embodiment described in this disclosure with one or more feature(s), element(s), or aspect(s) described in relation to any other one (or more) other embodiments described. These combinations include the incorporation of the features and/or aspect(s) of any dependent claim, singly or in combination with features and/or limitations of any one or more than one of the other dependent claims, with features and/or limitations of any one or more than one independent claim(s), with the remaining dependent claims in their original text being read and applied to any independent claim(s) so modified. These combinations also include combination of the features and/or limitations of one or more of the independent claims with features and/or limitations of another one or more than one of the independent claims to arrive at a modified independent claim, with the remaining dependent claims in their original text or alternately as modified per the foregoing, being read and applied to any independent claim(s) so modified. The compositions and methods of this invention are applicable to be used for inducing formation of granulation tissue on chemically-caused and electrically-caused third degree skin burns, in addition to third-degree skin burns caused by extreme thermal energy (heat) such as fire. Given the similarities between human skin and skin of other mammals, the present invention can be reasonably anticipated as being useful for treating third-degree burns on any other mammals whose epidermis repair mechanism sufficiently resembles that of humans.

Moreover, the present invention is particularly suited for cases involving persons having a large surface area of their skin affected by third degree burns. Within this disclosure some methods according to claim 1 involve the affected subject having multiple third-degree burn wounds to the extent that any amount between over 1% of their body's skin surface area and up to about 90% or more BSA is affected by third-degree burn wounds. In some embodiments the frequency of application can be at least once daily for any selected time period of between two days and eight weeks. In some embodiments, all of the person's third-degree burns are closed up and smooth, without keloid or scar formation at around the six week point after initial application of the topical compositions taught herein. In general, it is to be conservatively expected that at least 75% of the third-degree burns will in the vast majority of the cases be seen to have healed over smooth without keloid or scar formation within a time period of eight weeks following initial application of the topical composition comprising *Hamelia patens* extract.

The invention claimed is:

1. A method for inducing formation of visible granulation tissue on a third-degree burn wound on the skin of a human subject, said method comprising:
   a) providing a topical composition containing *Hamelia patens* extract in combination with a dermatologically-acceptable carrier; and
   b) contacting said composition topically to said third-degree burn wound in an effective amount and frequency of application for inducing the formation of visible granulation tissue,
   wherein new granulation tissue is visually observable in non-peripheral areas of said third-degree burn within 72 hours of initial application of said *Hamelia patens* extract to said wound.

2. A method according to claim 1 wherein said granulation tissue comprises multiple islands of granulation tissue.

3. A method according to claim 1 wherein said *Hamelia patens* extract comprises an extract made from only the leaves of the *Hamelia patens* plant.

4. A method according to claim 1 wherein said topical composition is applied to said third-degree burn at any frequency selected from the group consisting of: once daily, twice daily, three times daily and four times daily.

5. A method according to claim 1 wherein said dermatologically-acceptable carrier is in any form selected from the group consisting of: a salve, a cream, an ointment, a gel, and a lotion.

6. A method according to claim 1, wherein said dermatologically-acceptable carrier comprises an emulsion.

7. A method according to claim 1 wherein said dermatologically-acceptable carrier comprises any material selected from the group consisting of: water; saline solution, any C1 to C4 alcohol; any glyceryl ester oil; and any mineral oil, including any combinations of any of the foregoing.

8. A method according to claim 1 wherein said topical composition comprises a nanoparticle selected from the group consisting of: solid core nanoparticles, hollow core nanoparticles, lipid nanoparticles, polyethylene glycol nanoparticles, and chitosan nanoparticles, and including any mixtures of any of the foregoing.

9. A method according to claim 1 wherein said topical composition comprises a liposome.

10. A method according to claim 1 wherein said extract is selected from the group consisting of: an aqueous extract of *Hamelia patens*, a non-aqueous extract of *Hamelia patens*, an alcoholic extract of *Hamelia patens*, an aqueous-alcoholic extract of *Hamelia patens*, and any mixtures of the foregoing.

11. A method for inducing granulation tissue on a human subject suffering from third-degree skin burn wounds, wherein said subject suffers third-degree burn wounds over a surface area amount greater than 5% of their body's skin surface, and wherein said third-degree burn wounds are post-escharotomy burn wounds, comprising topical application of a *Hamelia patens* extract present in a dermatologically-acceptable carrier to the affected areas on the subject at least once daily for any selected time period of between two days and eight weeks.

* * * * *